United States Patent [19]

Smith et al.

[11] Patent Number: 5,006,595
[45] Date of Patent: Apr. 9, 1991

[54] SOLUBILIZATION OF COMPLEXES OF WATER-INSOLUBLE ORGANIC COMPOUNDS BY AQUEOUS SOLUTIONS OF POLYVINYLPYRROLIDONE

[75] Inventors: Terry E. Smith, Morristown; James R. Cho, Oakland; Ian W. Cottrell, Kinnelon, all of N.J.

[73] Assignee: GAF Chemicals Corporation, Wayne, N.J.

[21] Appl. No.: 414,673

[22] Filed: Sep. 29, 1989

Related U.S. Application Data

[62] Division of Ser. No. 161,888, Feb. 29, 1988, Pat. No. 4,900,775.

[51] Int. Cl.$^5$ .................................... C08L 37/00
[52] U.S. Cl. ............................ 524/548; 525/326.9; 525/359.1; 525/359.2; 525/359.3; 525/375
[58] Field of Search ................ 524/548; 525/326.9, 525/359.1, 359.2, 359.3, 375

[56] References Cited

U.S. PATENT DOCUMENTS

| | | | |
|---|---|---|---|
| 3,673,163 | 6/1972 | Walking | 424/80 X |
| 4,069,185 | 1/1978 | Sullivan | 524/548 |
| 4,151,185 | 4/1979 | Allcock et al. | 525/326.9 |
| 4,345,049 | 8/1982 | Denzinger et al. | 525/326.9 X |
| 4,433,112 | 2/1984 | Straub et al. | 525/387 X |
| 4,666,992 | 5/1987 | Barabas | 525/326.9 |
| 4,684,698 | 8/1987 | Barabas | 525/326.9 |
| 4,704,436 | 11/1987 | Barabas | 525/326.9 |

*Primary Examiner*—Joseph L. Schofer
*Assistant Examiner*—J. M. Reddick
*Attorney, Agent, or Firm*—McAulay, Fisher, Nissen, Goldberg & Kiel

[57] ABSTRACT

A method for increasing the water-solubility of highly insoluble organic compounds by forming a complex product from the reaction between the organic compound and an aqueous solution of solid polyvinylpyrrolidone. The solubility of the organic compound can be increased at least 25-fold and the complex formed is highly stable at ambient conditions.

17 Claims, No Drawings

SOLUBILIZATION OF COMPLEXES OF WATER-INSOLUBLE ORGANIC COMPOUNDS BY AQUEOUS SOLUTIONS OF POLYVINYLPYRROLIDONE

This is a divisional of application Ser. No. 07/161,888, filed Feb. 29, 1988 now U.S. Pat. No. 4,900,775.

BACKGROUND OF THE INVENTION

A major difficulty encountered with many organic compounds, particularly those of higher molecular weight and/or those having relatively complicated formulas, such as, pharmaceuticals, is that they are highly insoluble in water. This places significant limitations on the potential uses of these materials. For example, for those organic compounds which are used for industrial purposes, normally, a wide variety of organic solvents can be used. However, such solvents often present problems from the standpoint of cost and/or environmental impact. As a result, normally associated with the use of such organic solvents is the problem of their recovery so as to minimize the cost involved with their use, or their neutralization in the sense that the solvents no longer present an environmental or health hazard to humans or animals.

It is thus desirable that such compounds, rather than being utilized in organic solvents, be dissolved in water as the solvent. However, because of the nature of the organic compounds, it is often impossible to achieve a sufficiently high concentration of the organic material in water to facilitate the particular industrial use or chemical reaction desired.

This is particularly so with organic compounds which are used for agricultural purposes, such as, herbicides, pesticides, and the like. Thus, such compounds are normally applied to the plants and/or the earth in which the plants are growing and the best means of transporting the material into the plant or the earth is through water transport. However, because of the insolubility of many of these compounds, it is necessary to formulate them into emulsions or dispersions, usually in the presence of appropriate surface-activating agents, e.g., surfactants, and the like. The formulation of such emulsions increases the expense and manpower in the utilization of these agricultural chemicals. In addition, very often the efficiency of transport into the ecological system is not as high as desired. The ability to dissolve compounds of this nature in water in high concentrations would represent a significant achievement in this area of use.

With respect to pharmaceutical compounds, water is, of course, the solvent of choice. Indeed, it is normally impossible to use organic solvents as carriers for pharmaceuticals because of the toxicity associated with organic materials or solvents. Moreover, with pharmaceuticals which are used either for oral or injectable dosages, it is desired to have a higher rather than a lower concentration in water, since this decreases the particular amount of the material needed in any given dosage. Often, however, it is extremely difficult to obtain any significant or effective degree of solubility of such compounds in water so as to enhance their pharmaceutical efficacy.

In the past, it has been known that the use of polyvinylpyrrolidone could be used to increase the rate of dissolution of certain organic compounds in water. However, this art does not relate to an increase in solubility, but rather, only to an increase in the rate of dissolution. See L. M. Mortada, "Effect of Polyvinylpyrrolidone and Urea on Dissolution Rate of Phenylbutazone from Solid State Dispersion", Sci. Pharm. 48, 241–247 (1980); 0. I. Corregan, R. F. Timony and M. J. Whelan "The Influence of Polyvinylpyrrolidone on the Dissolution and Bioavailability of Hydrochlorothiazide", J. Phar. Pharmac. 28, 703 (1976); and R. Voight and D. Terborg, "Granulometric Determination of the Effect of PVP on Dissolution Rates of Sparingly Soluble Drugs", Pharmazie, 35, 311–312 (1980).

Numerous methods have been utilized for enhancing the solubility of complicated organic chemicals. For example, in U.S. Pat. No. 3,673,163, a method is described for the use of polyvinylpyrrolidone having molecular weights in excess of 1,000 by coprecipitating the polyvinylpyrrolidone with the drug Acronine. However, the increase in solubility obtained was only about 2.5 times the solubility of the compound. Such an increase in solubility for many of these compounds is not sufficient to render the use of the compound effective from a commercial or practical point of view.

Greater increases in solubility of highly insoluble organic compounds have been obtained as disclosed in application Ser. No. 106,845, filed Oct. 7, 1987. This has been accomplished by complexing the organic compound with a solid homopolymer or copolymer of N-vinyl-2-pyrrolidone having a molecular weight of greater than 1,000. In this method, a coprecipitation technique is used wherein solid N-vinyl-2-pyrrolidone and the organic compound are first dissolved in a mutual organic solvent and the solution is subjected to a complexing reaction. Thereafter, the solvent is removed, leaving the water-soluble complex. However, in certain instances, specific organic compounds do not exhibit as high a water-solubility of the complex as might be desired. Moreover, the method requires several steps, one of which is the removal of the solvent.

SUMMARY OF THE INVENTION

We have discovered a method for substantially increasing the water solubility of highly insoluble organic compounds in the range of at least 25 times the solubility of the compounds alone as measured at 25° C. at atmospheric pressure. Indeed, we have discovered a method for increasing the solubility of such compounds in many cases in excess of 100-times their original solubility. In addition, with the inventive method, in essence, only a single step is required, an organic solvent is not used, and there is no need to remove any solvent.

This is accomplished by forming a novel complex product from the reaction between the organic compound and an aqueous solution of solid polyvinylpyrrolidone having a weight greater than 1000 (all references to molecular weight, unless otherwise designated, refer to weight average molecular weight). The amount of polyvinylpyrrolidone solution and its concentration is adjusted merely to effect dissolution of the particular organic compound being reacted. Thus, the concentration of the aqueous polyvinylpyrrolidone solution is that which is effective to produce dissolution of the specific compound. The organic compound is suspended in the aqueous polyvinylpyrrolidone solution and is then heated with stirring at a temperature below the boiling point, e.g., approximately 100° C, and for a time to effect dissolution of the organic compound. This can be observed visually since when the solution is clear, the organic compound has been dissolved. Thereafter, the clear solution is allowed to cool to room temperature. This solution of the complexed organic compound can be used as is, or, if desired, water can be evaporated to produce a dry powder of the complex. The thus prepared aqueous solution of the complex exhibits prolonged stability at ambient temperatures.

DESCRIPTION OF THE PREFERRED EMBODIMENT

More particularly, the method of the present invention can be carried out by suspending the insoluble organic material in a solution of polyvinylpyrrolidone. The amount of the solution in terms of its volume or weight relative to the weight of the organic compound depends on the specific organic compound. Generally, however, the concentration of polyvinylpyrrolidone in the aqueous solution is in the range from about 20% to 75%, preferably from about 35% to 65%, and most preferably from about 40% to 50%. Polyvinylpyrrolidone having a weight average molecular weight in the range from about 2,500 to 1,100,000, and preferably, from about 2,500 to 49,000 is suitable for use in the invention. Most preferably, the molecular weight of the polyvinylpyrrolidone is from about 2,500 to 27,000. Generally, the weight ratio of the insoluble compound to polyvinylpyrrolidone is from 2:1 to about 1:300.

The suspension may be heated up to a temperature in the range from about 40° C. to 100° C, and preferably from about 60° C. to 85° C. This is carried out with mechanical stirring and the rate of heating, while not critical, is generally from about 0.05° C. to 2.0° C/minute, and preferably from about 1° C. to 2.0° C/minute. After reaching the desired temperature, it is maintained for a period of time to effect complete dissolution of the organic compound which is observed visually. When the solution is clear, the organic compound has been completely dissolved. Normally, the period of time is from about 0.5 to 8 hours, preferably, from about 0.5 to 1.5 hours, and most preferably from about 1.0 to 1.5 hours. The solution may be stirred during this heat treatment, i.e., during the period when the solution is maintained at a constant temperature.

Thereafter, the clear organic compound/polyvinylpyrrolidone solution is allowed to cool to ambient temperature. Normally, this is accomplished by letting the solution cool at ambient temperature. More rapid cooling can be effected by refrigeration although the rate of cooling is not critical. Generally, however, it is desired to avoid rapid cooling since it may result in supercooling and precipitation of the complex.

In an alternate method for the preparation of the complex of the present invention, the aqueous polyvinylpyrrolidone solution is first heated to a temperature between about 40° C. and 100° C, and preferably from about 60° C to 85° C. The insoluble organic compound is then gradually added to the hot aqueous polyvinylpyrrolidone solution with constant stirring. The mixture is then maintained at the appropriate temperature with stirring until all of the organic compound is dissolved and a clear solution is obtained.

Thereafter, the aqueous solution of the organic compound may be used as is. Alternately, the water may be removed, for example, by evaporation utilizing a rotary evaporator or the like, to produce a dry powder of the complex. This can then be redissolved in water as desired.

In yet another embodiment of the invention, the insoluble organic compound may first be dissolved in an organic solvent which is miscible with water, e.g., ethanol. This solution is then added to an aqueous solution of polyvinylpyrrolidone. The organic solvent is then removed by evaporation.

A wide variety of substantially water insoluble organic compounds may be used for forming the complexes of the present invention. Such compounds are disclosed in U.S. Pat. No. 4,666,992, and copending applications Ser. Nos. 858,778, filed May 2, 1986 now U.S. Pat. No. 4,758,674; 858,635, filed May 2, 1986 now U.S. Pat. No. 4,713,238; 858,976, filed May 2, 1986 now abandoned; 849,918, filed Apr. 9, 1986 now U.S. Pat. No. 4,684,519; 858,977, filed May 2, 1986 now U.S. Pat. No. 4,704,436; and 858,978, filed May 2, 1986 now U.S. Pat. No. 4,684,698, the disclosures of all of which are incorporated herein by reference.

As used herein, the expression "substantially insoluble" means that the solubility of the compound in water is so low as to render its use in aqueous solution impractical or highly inefficient, e.g., for insoluble pharmaceuticals.

In addition to the compounds disclosed in the above patents and/or copending applications, we have discovered that additional insoluble compounds may be treated using the present invention. In particular, those compounds which are especially adapted for hydrogen bonding, polar bonding, hydrophobic bonding, ionic bonding, and bonding by van der Waals forces are highly susceptible to complexing with the polyvinylpyrrolidone utilized in the present invention to produce complexes exhibiting solubilities which are extremely high multiples of the solubility of the original organic compound.

The following examples illustrate the present invention:

Example 1:

Furosemide (5.0 g) was suspended in 100 g 50% polyvinylpyrrolidone having a molecular weight of approximately 10,000 (GAF PVP K-15) aqueous solution. The mixture was heated to 85° C. with mechanical stirring and the temperature was maintained at 85° C. for 1.5 hours. The clear drug/PVP solution was slowly cooled to room temperature. The concentration of the drug was calculated to be 10% (g drug/100 g water). The initial solubility of Furosemide in water at room temperature was 0.0037%.

Example 2

Furosemide (0.5 g) was dissolved in 30 g of absolute ethanol by gently heating in a 45° C. bath. 25 g of polyvinylpyrrolidone having a molecular weight of approximately 10,000 (GAF PVP K-15) was dissolved in 25 g distilled water. The solution was heated to 45° C. and then a vacuum was applied until the solution began to boil. The ethanol was then azeotroped out by distillation and an equal amount of water was added to the solution to maintain the original volume and concentration. This ultimately resulted in exchange of the ethanol with the water in a mixture. The alcoholic Furosemide solution was added dropwise to the PVP aqueous solution over a period of 30 minutes.

Example 3

1 g of Furosemide was suspended in 21.5 g methanol and the mixture was added to 20 g of 50% polyvinylpyrrolidone having a molecular weight of approximately 10,000 (GAF PVP K-15) aqueous solution. The drug/PVP solution was split into two equal portions. One portion was solvent exchanged with water at 80-85° C. The methanol was exchanged from the solution in the same manner as in Example 2. The final 50% aqueous PVP/drug solution was clear and no precipitation occurred after one week after 1- to 4-fold dilutions. The second portion was solvent exchanged with water at below 40° C. in the manner described in Example 2. The final 50% PVP/drug aqueous solution was stable for more than one week after 1- to 4-fold dilutions with water. Furosemide/PVP complex could be recovered in powder form by evaporation of water at 40-45° C. under vacuum. The aqueous Furosemide solution prepared from this dry powder complex was clear at drug concentrations of 3.4% and 11% (g drug/100 g water).

Example 4

This example compares the aqueous PVP solution method with the coprecipitation method. 1 g of Furosemide was dissolved in 50 g ethanol and 10 g of polyvinylpyrrolidone having a molecular weight of approximately 10,000 (GAF PVP K-15) was dissolved in 50 g ethanol. The alcoholic drug and PVP solutions were mixed dropwise over a period of one hour. The final solution was evaporated on a rotary evaporator at 75° C. to dryness. The drug/PVP complex was recovered as a dry powder. The complex (0.5 g), composed of 0.05 g drug and 0.45 g PVP, was stirred in 0.5 g water to give a hazy solution, in contrast to the clear solution obtained with the procedure described in Example 1.

Example 5

Chlorhexidine, 0.05 g, was suspended in 5.0 g 40% polyvinylpyrrolidone having a molecular weight of approximately 10,000 (GAF PVP K-15) aqueous solution. The drug/PVP mixture was heated at 85° C. for 1.5 hours and left to slowly cool to room temperature. The clear chlorhexidine/PVP aqueous solution was stable without precipitation for over one week at room temperature. The drug/PVP solution was diluted fourfold and ten-fold with water. No precipitation occurred with either of these dilutions.

Example 6

Chlorhexidine, 0.3 g, was suspended in 5.0 g of 50% PVP K-15 aqueous solution and heated at 85° C. for 1.5 hours with continuous stirring. The resultant clear solution was slowly cooled to room temperature. The solution was stable without precipitation for over a week. The concentrated drug/PVP solution was diluted with water from 1 to 4-fold 10-fold the original volume. The diluted drug solutions were stable at room temperature for one week.

Example 7

This example compares the coprecipitation method to the present invention. Chlorhexidine, 0.50 g, was suspended in 20 g absolute ethanol and added to 20.8 g of 20% PVP K-15 ethanol solution. After the drug was completely dissolved the solution was rotoevaporated at 45° C. under vacuum over a period of 2 hours. The drug/PVP complex was recovered as a dry powder. The complex, 0.5 g, composed of 0.054 g drug and 0.446 g PVP, was mixed with 0.5 g water and placed on a mechanical shaker for 2 hours. The final solution was hazy and contained some insoluble material. The ratio of chlorhexidine/PVP was 1/8.3 similar to the drug/PVP ratio of Example 6.

Example 8

Trifluralin ($\alpha,\alpha,\alpha$-trifluoro-2,6-dinitro-N,N-dipropyl-p-toluidine), a non-ionic herbicide having a low water solubility of 0.3 ppm was solubilized in the following manner: 0.02 g of trifluralin was suspended in 2.0 g of 50% polyvinylpyrrolidone (GAF PVP K-15) in aqueous solution. The mixture was heated to a temperature from 80° C. to 90° C. for one hour with continuous stirring. The mixture was then allowed to cool to room temperature. The final solution was slightly hazy and stable upon standing at room temperature and no precipitation was observed for a period of more than a week.

What is claimed is:

1. A method for preparing a water-soluble complex of a water-insoluble organic compound selected from the group consisting of furosemide, chlorhexidine, and trifluralin consisting essentially of heating an aqueous solution of polyvinylpyrrolidone to a temperature between about 40° C. and 100° C., admixing the insoluble organic compound to the heated polyvinyl-pyrrolidone solution and maintaining the mixture at the heating temperature until the organic compound is dissolved.

2. The method of claim 1 wherein the polyvinylpyrrolidone has a weight average molecular weight of more than 1000.

3. The method of claim 1 wherein after dissolution, the water is removed to yield the complex in dry form.

4. The method of claim 1 wherein the concentration of the polyvinylpyrrolidone is in the range from about 20% to 75% by weight.

5. The method of claim 1 wherein the polyvinylpyrrolidone has a weight average molecular weight in the range from about 2,500 to 1,100,000.

6. The method of claim 1 wherein the polyvinylpyrrolidone has a weight average molecular weight in the range from about 2,500 to 27,000.

7. The method of claim 1 wherein the heating period is from about 0.5 to 1.5 hours.

8. The method of claim 1 wherein after the heating period, the solution is cooled to room temperature.

9. A method for preparing a water-soluble complex of a water-insoluble organic compound selected from the group consisting of furosemide, chlorhexidine, and trifluralin consisting essentially of dissolving the organic compound in a solvent which is miscible with water, admixing the solution with a solution of polyvinylpyrrolidone in water and removing the organic solvent from the mixture.

10. The method of claim 9 wherein the organic solvent is ethanol or methanol.

11. The method of claim 10 wherein the mixture is evaporated to remove the solvent.

12. The method of claim 9 wherein the concentration of the organic compound in the organic solvent is in the range from about 1% to about 50%.

13. The method of claim 9 wherein the concentration of the polyvinylpyrrolidone in the water is in the range from about 20% to 75% by weight.

14. The method of claim 9 wherein the polyvinylpyrrolidone has a weight average molecular weight of more than 1000.

15. The method of claim 9 wherein the polyvinylpyrrolidone has a weight average molecular weight in the range from about 2,500 to 1,100,000.

16. The method of claim 9 wherein the polyvinylpyrrolidone has a weight average molecular weight in the range from about 2,500 to 27,000.

17. The method of claim 9 wherein after the removal of the organic solvent, the water is removed to yield the complex in dry form.

* * * * *